United States Patent
Gracey et al.

(10) Patent No.: US 8,329,960 B2
(45) Date of Patent: *Dec. 11, 2012

(54) PROCESS FOR THE CONVERSION OF HYDROCARBONS TO OXYGENATES

(75) Inventors: Benjamin Patrick Gracey, East Riding of Yorkshire (GB); Michael Keith Lee, East Riding of Yorkshire (GB)

(73) Assignee: BP Chemicals Limited, Middlesex (GB)

( * ) Notice: Subject to any disclaimer, the term of this patent is extended or adjusted under 35 U.S.C. 154(b) by 415 days.

This patent is subject to a terminal disclaimer.

(21) Appl. No.: 12/311,940

(22) PCT Filed: Oct. 17, 2007

(86) PCT No.: PCT/GB2007/003974
§ 371 (c)(1),
(2), (4) Date: Apr. 20, 2009

(87) PCT Pub. No.: WO2008/047125
PCT Pub. Date: Apr. 24, 2008

(65) Prior Publication Data
US 2009/0292148 A1    Nov. 26, 2009

(30) Foreign Application Priority Data

Oct. 20, 2006 (EP) .................................. 06255402

(51) Int. Cl.
*C07C 27/12* (2006.01)
(52) U.S. Cl. .................. 568/885; 568/955; 518/705
(58) Field of Classification Search .................. 568/885, 568/955; 518/705
See application file for complete search history.

(56) References Cited

U.S. PATENT DOCUMENTS

| | | |
|---|---|---|
| 4,218,389 A | 8/1980 | Jackson et al. |
| 4,464,483 A | 8/1984 | De Lathouder |
| 4,546,111 A | 10/1985 | Banquy |
| 6,225,359 B1 | 5/2001 | O'Rear et al. |
| 2005/0197412 A1 | 9/2005 | Van Egmond et al. |

FOREIGN PATENT DOCUMENTS

| | | |
|---|---|---|
| EP | 0 253 540 | 1/1988 |
| GB | 2 162 172 | 1/1986 |
| WO | WO 2005/108336 | 11/2005 |

OTHER PUBLICATIONS

International Search Report for PCT/GB2007/003974, mailed Jan. 24, 2008.
Written Opinion of the International Searching Authority for PCT/GB2007/003974, mailed Jan. 24, 2008.

*Primary Examiner* — Sikarl Witherspoon
(74) *Attorney, Agent, or Firm* — Nixon & Vanderhye

(57) ABSTRACT

Process for converting a hydrocarbon feedstock into alcohol(s), wherein the hydrocarbons are first converted into syngas, which is subsequently converted into alcohols. The process comprises the consecutive steps of 1) converting a hydrocarbon feedstock, in a syngas reactor, into a stream A, comprising essentially of a mixture of carbon oxide(s) and hydrogen, 2) converting at least part of stream A, in the presence of a catalyst in a oxygenate synthesis reactor under a temperature comprised between 150 and 400° C. and a pressure of 20 to 200 bar, into an alcohols stream B, comprising essentially methanol, ethanol, propanol(s), H2, C1-03 alkanes, CO, CO2 and water, 3) separating stream B, into a stream C containing the CO, C1-C3 alkanes, H2 and methanol; a stream D containing the CO2; and recovering a stream E containing the ethanol, propanol(s) and water, 4) treating a fraction of stream C in order to separate said fraction into a stream comprising CO, and a stream comprising H2 and the C1-C3 alkanes, 5) reintroducing at least part of stream C together with the stream comprising CO from step 4 into the oxygenate synthesis reactor of step 2, and 6) reintroducing at least part of stream D into the syngas reactor of step 1.

22 Claims, 2 Drawing Sheets

PROCESS FOR THE CONVERSION OF HYDROCARBONS TO OXYGENATES

This application is the U.S. national phase of International Application No. PCT/GB2007/003974 filed 17 Oct. 2007, which designated the U.S. and claims priority to Europe Application No. 06255402.7 filed 20 Oct. 2006, the entire contents of each of which are hereby incorporated by reference.

The present invention relates to an improved process, that has a significantly reduced level of carbon oxide(s) emissions, for the conversion of hydrocarbons into alcohol(s), wherein the hydrocarbons are first converted into syngas which is then subsequently converted into alcohol(s) in the presence of a catalyst.

In particular, the present invention relates to an improved process, that has a significantly reduced level of carbon oxide(s) emissions, for the conversion of hydrocarbons into alcohol(s), wherein the hydrocarbons are first converted into syngas, which is then subsequently converted into alcohol(s) in the presence of a modified molybdenum sulphide based catalyst, or a modified methanol based catalyst and/or a modified Fischer-Tropsch catalyst and/or a supported rhodium catalyst.

BACKGROUND OF THE INVENTION

In recent years increased use and demand for alcohols such as methanol, ethanol and higher alcohols has led to a greater interest in processes relating to alcohol production. The said alcohols may be produced by the fermentation of, for example, sugars and/or cellulosic materials.

Alternatively, alcohols may be produced from synthesis gas. Synthesis gas refers to a combination of hydrogen and carbon oxides produced in a synthesis gas plant from a carbon source such as natural gas, petroleum liquids, biomass and carbonaceous materials including coal, recycled plastics, municipal wastes, or any organic material. Thus, alcohol and alcohol derivatives may provide non-petroleum based routes for the production of valuable chemicals and fuels.

Generally, the production of alcohols, for example methanol, takes place via three process steps: synthesis gas preparation, methanol synthesis, and methanol purification. In the synthesis gas preparation step, an additional stage maybe employed by where the feedstock is treated, e.g. the feedstock is purified to remove sulphur and other potential catalyst poisons prior to being converted into synthesis gas. This treatment can also be conducted after syngas preparation; for example, when coal or biomass is employed.

The reaction to produce alcohol(s) from syngas is generally exothermic. The formation of C2 and C2+ alcohols is believed to proceed via the formation of methanol for modified methanol catalysts and cobalt molybdenum sulphide catalysts. However, the production of methanol is equilibrium limited and thus requires high pressures in order to achieve viable yields. Hence, pressure can be used to increase the yield, as the reaction which produces methanol exhibits a decrease in volume, as disclosed in U.S. Pat. No. 3,326,956. Improved catalysts have now allowed viable rates of methanol formation to be achieved at reduced reaction temperatures, and hence allow commercial operation at lower reaction pressures, e.g. a copper oxide-zinc oxide-alumina catalyst that typically operates at a nominal pressure of 5-1 MPa and temperatures ranging from approximately 150 DEG C. to 450 DEG C. over a variety of catalysts, including $CuO/ZnO/Al_2O_3$, $CuO/ZnO/Cr_2O_3$, $ZnO/Cr_2O_3$, and supported Fe, Co, Ni, Ru, Os, Pt, and Pd catalysts. A low-pressure, copper-based methanol synthesis catalyst is commercially available from suppliers such as BASF, ICI Ltd. of the United Kingdom, and Haldor-Topsoe. Methanol yields from copper-based catalysts are generally over 99.5% of the converted CO+CO2 present. Water is a by-product of the conversion of CO2 to methanol and the conversion of CO synthesis gas to C2 and C2+ oxygenates. In the presence of an active water gas-shift catalyst, such as a methanol catalyst or a cobalt molybdenum catalyst the water equilibrates with the carbon monoxide to give CO2 and hydrogen. A paper entitled, "Selection of Technology for Large Methanol Plants," by Helge Holm-Larsen, presented at the 1994 World Methanol Conference, Nov. 30-Dec. 1, 1994, in Geneva, Switzerland, reviews the developments in methanol production and shows how further reduction in costs of methanol production will result in the construction of very large plants with capacities approaching 10,000 metric tonnes per day.

Other processes, for the production of C2 and C2+ alcohol(s), include the processes described hereinafter; U.S. Pat. No. 4,122,110 relates to a process for manufacturing alcohols, particularly linear saturated primary alcohols, by reacting carbon monoxide with hydrogen at a pressure between 20 and 250 bars and a temperature between 150 DEG and 400 DEG C., in the presence of a catalyst, characterized in that the catalyst contains at least 4 essential elements: (a) copper (b) cobalt (c) at least one element M selected from chromium, iron, vanadium and manganese, and (d) at least one alkali metal.

U.S. Pat. No. 4,831,060 relates to the production of mixed alcohols from carbon monoxide and hydrogen gases using a catalyst, with optionally a co-catalyst, wherein the catalyst metals are molybdenum, tungsten or rhenium, and the co-catalyst metals are cobalt, nickel or iron. The catalyst is promoted with a Fischer-Tropsch promoter like an alkali or alkaline earth series metal or a smaller amount of thorium and is further treated by sulfiding. The composition of the mixed alcohols fraction can be selected by selecting the extent of intimate contact among the catalytic components.

Journal of Catalysis 114, 90-99 (1988) discloses a mechanism of ethanol formation from synthesis gas over $CuO/ZnO/Al_2O_3$. The formation of ethanol from CO and H2 over a CuO/ZnO methanol catalyst is studied in a fixed-bed microreactor by measuring the isotopic distribution of the carbon in the product ethanol when 13C methanol was added to the feed.

At present, there are two major issues, associated with the conversion of hydrocarbons to alcohol(s), which need to be addressed.

The first issue is primarily an environmental concern, as when manufacturing and using syngas as part of an integrated process, the high temperatures necessary for syngas formation, are often generated by the burning of carbonaceous fuel, and hence dilute carbon dioxide is produced as a result.

In addition to this, is the fact that water is produced as a result of the conversion of syngas to C2 and C2+ alcohol(s), which consequently is rapidly converted to carbon dioxide and hydrogen during the oxygenate synthesis reaction stage due to the nature of the typical catalysts used (i.e. active water gas-shift catalysts), and the reaction conditions typically employed in these processes. Hence, during the overall integrated process, significant amounts of carbon dioxide is produced and emitted into the environment.

Contributing significantly to the above issue, is the factor that the use of a typical higher alcohol catalysts during the alcohol synthesis stage of the process, results in the build up of alkanes (due to loss of selectivity) during the required gas recycling process, which will often necessitate in a purge.

Typically purge streams are fuelled or flared which can add significant amounts of CO2 to the overall carbon emissions.

The level of carbon dioxide present in the atmosphere is a well documented environmental concern of today's world, as carbon dioxide is considered to be the most prominent of all the 'greenhouse gases', and therefore one of the main pollutants in the present atmosphere. For this reason, it is of global interest and concern to reduce carbon dioxide emissions in industrial processes to a minimum as far as possible.

The second issue associated with the conversion of hydrocarbons to alcohol(s), wherein the hydrocarbons are first converted into syngas, which is then subsequently converted into alcohol(s), is concerned with the overall heat efficiency of the process. Historically, there has been a lot of interest shown in trying to utilise the heat generated during the syngas to alcohol(s) conversion stage efficiently, for example by generating steam from the excess heat and subsequently using the steam to provide the energy to power alternative processes. However, depending on the production site in question, this is not always possible. Therefore, recently more interest has been shown in trying to improve efficiency of the heat generated in a more local manner, i.e. as part of an integrated process.

SUMMARY OF THE INVENTION

It is therefore an object of the present invention to address the above issues, and to provide an improved process in terms of CO2 emissions and energy efficiency for the conversion of hydrocarbons into alcohols, wherein the hydrocarbons are first converted into syngas, which is subsequently converted into alcohols.

In particular, the present invention relates to an improved process in terms of CO2 emissions and energy efficiency for the conversion of hydrocarbons into alcohols, wherein the hydrocarbons are first converted into syngas, which is subsequently converted into alcohols preferably in the presence of a modified molybdenum sulphide based catalyst, or a modified methanol based catalyst and/or a modified Fischer-Tropsch catalyst and/or a supported rhodium catalyst.

DETAILED DESCRIPTION OF PREFERRED EMBODIMENTS

Figure 1:
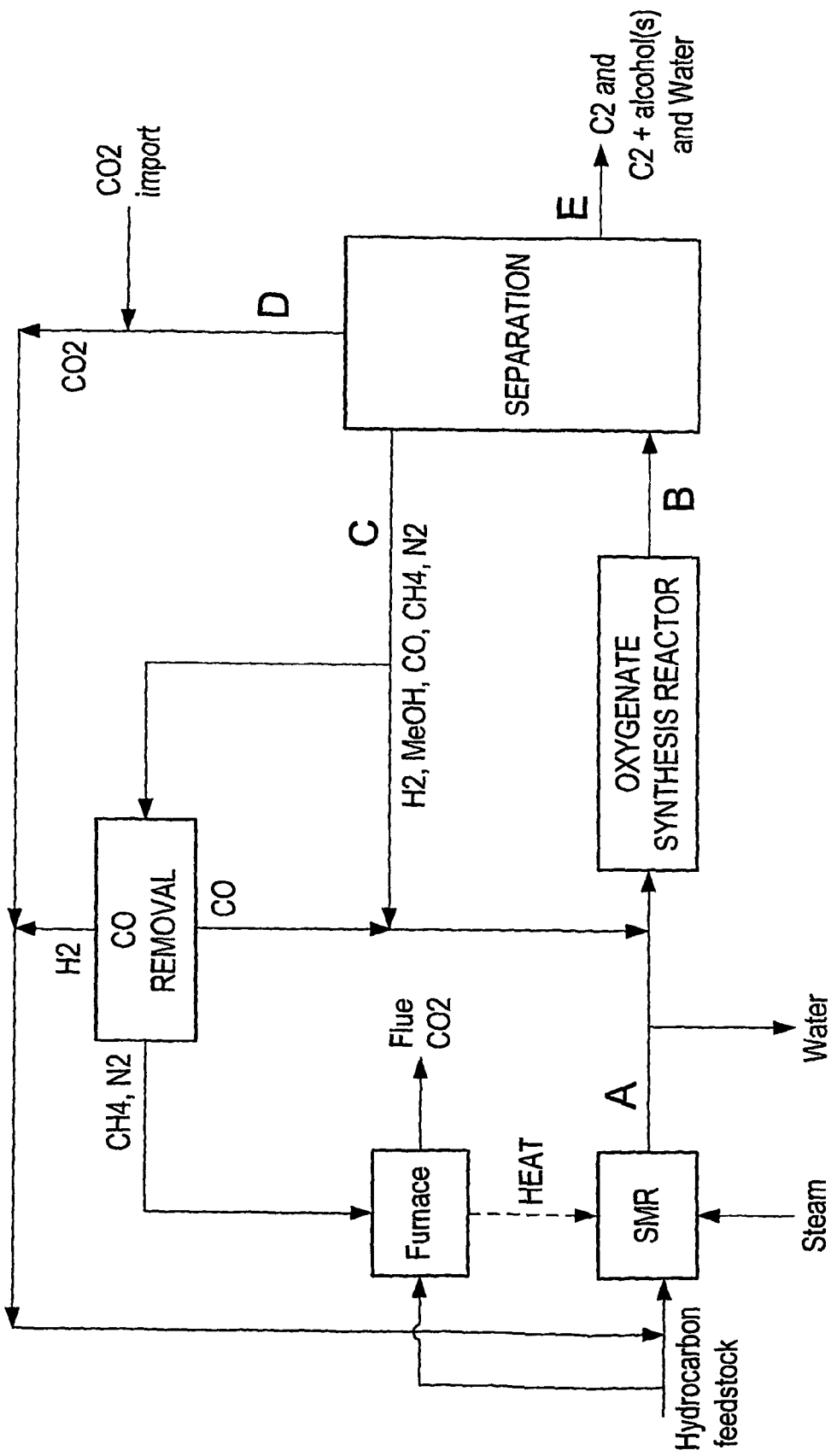
FIG. 1, represents one embodiment of a process scheme according to the present invention. This said embodiment comprises process steps according to the present invention. The letter references in FIG. 1 correspond to those used in the present description and appending claims.
Figure 2:
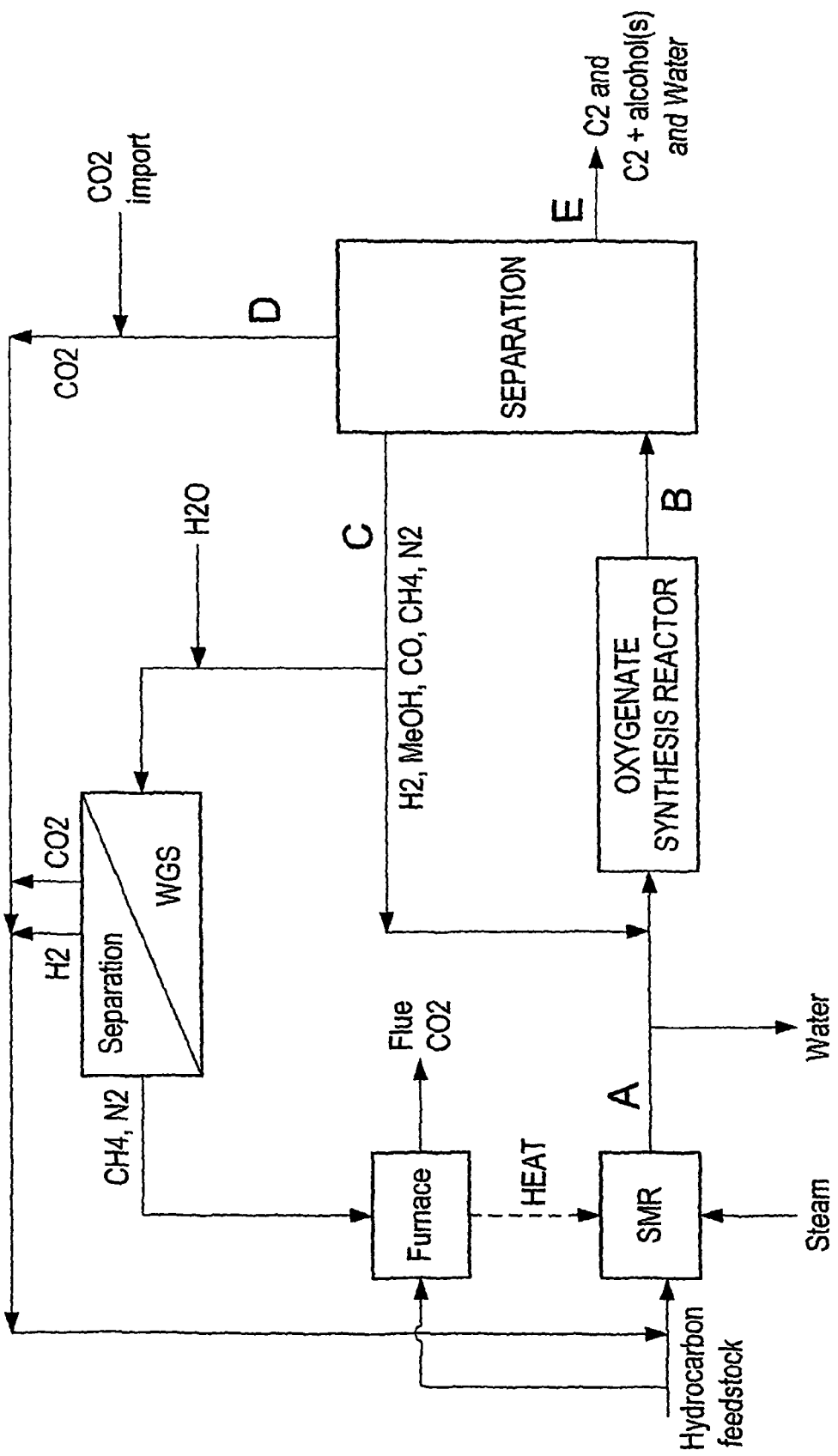
FIG. 2, represents another embodiment of a process scheme according to the present invention. This said embodiment comprises optional and/or preferred process steps according to the present invention. The letter references in FIG. 2 correspond to those used in the present description and appending claims.

The present invention thus provides a process for the conversion of a hydrocarbon feedstock into alcohol(s), wherein the hydrocarbons are first converted into syngas, which is subsequently converted into alcohols, characterised by the following consecutive steps:
1. converting a hydrocarbon feedstock, in a syngas reactor, into a stream A, comprising essentially of a mixture of carbon oxide(s) and hydrogen,
2. converting at least part of stream A, in the presence of a catalyst in a oxygenate synthesis reactor under a temperature comprised between 150 and 400° C. and a pressure of 20 to 200 bar, into an alcohols stream B, comprising essentially methanol, ethanol, propanol(s), H2, C1-C3 alkanes, CO, CO2 and water,
3. separating stream B, into a stream C containing the CO, C1-C3 alkanes, H2 and methanol; a stream D containing the CO2; and recovering a stream E containing the ethanol, propanol(s) and water,
4. treating a fraction of stream C in order to separate said fraction into a stream comprising CO, and a stream comprising H2 and the C1-C3 alkanes,
5. reintroducing at least part of stream C together with the stream comprising CO from step 4 into the oxygenate synthesis reactor of step 2, and
6. reintroducing at least part of stream D into the syngas reactor of step 1.

The term 'target alcohols', as used herewith and hereinafter, is understood to mean the alcohols produced (stream E) according to the process described by the present invention and preferably consist of either ethanol or propanol(s) or, more preferably, a mixture thereof.

The hydrocarbon feedstock used for syngas generation is preferably a carbonaceous material, for example biomass, plastic, naphtha, refinery bottoms, crude syngas (from underground coal gasification or biomass gasification), smelter off gas, municipal waste, coal, and/or natural gas, with coal and natural gas being the preferred sources, and natural gas being the most preferable source.

Natural gas commonly contains a range of hydrocarbons (e.g. C1-C3 alkanes), in which methane predominates. In addition to this, natural gas will usually contain nitrogen, carbon dioxide and sulphur compounds. Preferably the nitrogen content of the feedstock is less than 40 wt %, more preferably less than 10 wt % and most preferably less than 1 wt %.

Processes for producing mixtures of carbon oxide(s) and hydrogen (synthesis gas), in a syngas reactor, are well known. Each method has its advantages and disadvantages, and the choice of using a particular reforming process is dictated by economic and available feed stream considerations, as well as obtaining the desired mole ratio of H2:CO in the feedstock resulting from the reforming reaction. A discussion of the available synthesis gas production technologies is provided in both "Hydrocarbon Processing" V78, N. 4, 87-90, 92-93 (April 1999) and "Petrole et Techniques", N. 415, 86-93 (July-August 1998), and are hereby incorporated by reference. It is also known that the synthesis gas may be obtained by catalytic partial oxidation of hydrocarbons in a microstructured reactor as exemplified in "IMRET 3: Proceedings of the Third International Conference on Microreaction Technology", Editor W Ehrfeld, Springer Verlag, 1999, pages 187-196. Alternatively, the synthesis gas may be obtained by short contact time catalytic partial oxidation of hydrocarbonaceous feedstocks as described in EP 0303438. The synthesis gas can also be obtained via a "Compact Reformer" process as described in "Hydrocarbon Engineering", 2000, 5, (5), 67-69; "Hydrocarbon Processing", 79/9, 34(September 2000); "Today's Refinery", 15/8, 9 (August 2000); WO 99/02254; and WO 200023689.

The syngas used in the present invention is preferably obtained via a steam reforming. Typically, for commercial syngas production the pressure at which the synthesis gas is produced ranges from approximately 1 to 100 bar, preferably 20 to 30 bar and the temperatures at which the synthesis gas exits the reformer ranges from approximately 700 DEG C. to 1000 DEG C. The high temperatures are necessary in order to produce a favourable equilibrium for syngas production, and to avoid metallurgy problems associated with carbon dusting. The synthesis gas used in the present invention preferably contains a molar ratio of (H2-CO2):(CO+CO2) ranging from 0.8 to 3.0, which is heavily dependent on the hydrocarbon feedstock used. When natural gas is used as the hydrocarbon feedstock, the syngas obtained has a (H2-CO2):(CO+CO2) maximum ratio of 3.

The steam reforming reaction is a highly endothermic in nature. The reaction is commonly catalysed within tubes of a reformer furnace. Where natural gas is the feedstock, the endothermic heat is usually supplied externally by firing additional amounts of natural gas. Simultaneous to the steam reforming reaction, the water/gas shift reaction also takes place. The presence of a catalyst in this reaction commonly requires a de-sulphurised feedstock, as sulphur compounds are known poisons for the typical catalysts employed. The steam reformer requires a high steam to carbon ratio to prevent carbon from being deposited on the catalyst and also to ensure high conversion to carbon monoxide and the preferred molar ratio of steam to carbon (i.e. the carbon that is present as hydrocarbons) is between 1 and 2.5, preferably between 1.2 and 2 and most preferably between 1.4 and 1.8.

According to a preferred embodiment of the present invention, the hydrocarbon feedstock fed into the syngas reactor is preheated to a temperature comprised between 400 and 550 DEG C, and more preferably the preheated temperature is such that it alleviates the formation of metal dusting (i.e. a temperature that is as close to 550 DEG C as possible). The use of a furnace(s) may be employed to generate the energy required to preheat the hydrocarbon feedstock prior to entering the syngas reactor. Alternatively, an interchanger may be employed in addition to the furnace(s), whereby the heat generated from cooling the product from the syngas reactor (stream A), is then used to preheat the hydrocarbon feedstock entering into the syngas reactor, thereby reducing the duty on the furnace and increasing the overall heat efficiency of the process. Whilst use of the interchanger is the preferred method of operation, it should be noted that stream A must be rapidly cooled (e.g. by preferably using a fluid) to prevent metal dusting; hence the maximum temperature of the cold-side fluid (e.g. water) used to cool the exit stream is approximately 500 DEG C. The preferred method of cooling stream A is against a boiling fluid, such as water.

According to the present invention, the exit stream obtained from the syngas reactor (e.g. using a steam reformer), stream A, comprises essentially a mixture of carbon oxide(s) and hydrogen. It can also comprise water, nitrogen and traces of unconverted hydrocarbon (e.g. C1-C3 alkanes). The stream A is then preferably cooled further to a temperature that is comprised between 5 and 60 DEG C, and more preferably to a temperature that is comprised between 20 and 50 DEG C. Once this temperature has been achieved, then the majority of the water is preferably removed from stream A and the overall water content of the treated stream A, after water removal treatment, is less than 5% wt of stream A, more preferably less than 1% wt of stream A and most preferably treated stream A contains less than 0.5% wt of water.

Treated stream A is then preferably pre-heated, by use of a furnace(s) and/or any other suitable method known to those skilled in the art, to a temperature that is comprised between the operating temperature of the oxygenate synthesis reactor and (or equal to) 30 DEG C less than the operating temperature of the oxygenate synthesis reactor, more preferably treated stream A is pre-heated to a temperature that is as close to the operating temperature of the oxygenate synthesis reactor as possible.

In one embodiment of this invention at least part, preferably all of stream A comprising the desired synthesis gas molar ratio of (H2):(CO) is fed into the oxygenate synthesis reactor at a controlled rate and the reaction is carried out in a reaction zone under controlled conditions of temperature and pressure and in the presence of a catalyst to convert the feedstock into the target alcohols.

According to the present invention, the desired synthesis gas molar ratio (defined as being H2/CO) of the total feed introduced into the oxygenate synthesis reactor of step 2, is preferably comprised between 0.5 and 2.0, more preferably comprised between 0.5 and 1.5.

According to a preferred embodiment of the present invention, stream A is passed through a H2/CO2 membrane prior to entering the oxygenate synthesis reactor.

The H2/CO2 membranes that can be used according to the present invention are preferably membranes based on a polymer packaged as a hollow fibre. A differential pressure is established across the said membrane. All gases permeate from the high-pressure (feed) side of the membrane to the low-pressure (permeate) side, and the difference in the permeation rates of gases provides the separation. Molecules that permeate quickly, such as H2, He, and H2S, can be separated from molecules that permeate more slowly, such as CO, CH4 and N2. Such membrane technologies can be found in 'Purification and Recovery Options for Gasification' D. J. Kubek, E. Polla, F. P. Wilcher, UOP, 1996, and are hereby incorporated by reference.

Optionally, after the gas is passed through the membrane some remixing of the permeate with the retained material may be employed in order to adjust the syngas ratio to achieve the optimum ratio required for the oxygenate synthesis reaction.

The oxygenate synthesis reaction (alcohol(s) synthesis), according to step 2 of the present invention, is preferably performed by passing a mixture of hydrogen and carbon monoxide (stream A) over a conversion catalyst as a vapour phase reaction (e.g. using a fixed bed and/or fluidized bed reactor) or as a liquid phase reaction in an essentially involatile and inert solvent, such as a hydrocarbon (e.g. using a slurry reactor).

The said oxygenate synthesis reaction (the alcohol synthesis) may be carried out in a oxygenate synthesis reactor, under conditions as indicated in step 2. The term oxygenate synthesis reactor as used in the present invention pertains to any appropriate reactor, e.g. a tubular reactor using a fixed bed of the catalyst. The reactants may be fed upwards or downwards to the catalyst, or a combination of both, to a fixed bed located in a tubular reactor. The reaction may be effected in a dynamic bed of the catalyst. In such a reaction, the bed of catalyst is moving such as in the case of a fluid bed of the catalyst. The oxygenate synthesis reactor may preferably be chosen amongst tubular, multitubular, slurry, moving bed, fluidised bed, radial bed, multibed or reactive distillation reactor. According to an embodiment of the present invention, a fixed bed reactor is used, preferably a radial bed(s) or a multitubular vapour phase reactor or a combination thereof is used. Most preferably the oxygenate synthesis reactor comprises a series of adiabatic fixed bed reactors operated in either a longitudinal and/or radial flow mode.

According to a preferred embodiment of the present invention, the alcohol(s) produced in the oxygenate synthesis reactor (i.e. during alcohol synthesis) are primarily methanol, ethanol, propanol(s) (n-propanol with low amounts of iso-propanol), and butanol(s) (n-butanol and iso-butanol); said methanol, ethanol, propanol(s) and butanol(s) preferably represent together at least 50% by carbon content of the products (where the products are defined as being all products excluding $CO_2$ and CO) obtained from the oxygenate synthesis reactor (stream B), more preferably at least 75% by carbon content of the products obtained and most preferably at least 80% by carbon content of the products obtained.

According to another embodiment of the present invention esters and ethers are also produced in the oxygenate synthesis reactor and together with the alcohol(s) on a single pass, preferably represent at least 70% by carbon content of the products (where the products are defined as being all products excluding $CO_2$ and CO) obtained from the oxygenate synthesis reactor (stream B), more preferably at least 80% by carbon content of the products obtained and most preferably at least 85% by carbon content of the products obtained. Stream B also typically contains a level of nitrogen, which arises as an impurity from the aforementioned hydrocarbon feedstock(s), together with a level of hydrocarbons (e.g. C1-C3 alkanes(s)) that arise from incomplete conversion in the reforming stage and as reaction by-products during the oxygenate synthesis reaction.

According to a preferred embodiment of the present invention the quantity of inert materials with respect to the oxygenate synthesis reaction (e.g. C1-C3 alkanes and nitrogen) present in stream B, during normal operation, is less than 30 mol % of stream B and preferably less than 20 mol % of stream B.

The C2 and C3 target alcohols comprise together, at least 25% by carbon content of the products (where the products are defined as being all products excluding $CO_2$ and CO), obtained from the oxygenate synthesis reactor (stream B), preferably at least 33% by carbon content of the products obtained and most preferably at least 50% by molar carbon content of the products obtained.

In a preferred embodiment of the present invention, the conversion of the carbon oxide(s) per pass through the oxygenate synthesis reactor is set to operate between 5 and 70%, preferably between 10 and 50% and most preferably between 15 and 40%, as the applicants have found this to be the most advantageous conversion rate in terms of sufficient productivity of the target alcohol(s) per pass whilst maintaining reduced overall alkane production. Conversions per pass, higher than those stated above are covered by the present invention; however they do not represent preferred embodiments of the present invention since they lead to the undesirable formation of alkanes as part of the integrated process.

The temperature in the oxygenate synthesis reaction zone is approximately between 150 and 400 DEG C, preferably between 250 and 350 DEG C and most preferably between 280 and 320 DEG C.

The pressure employed in the oxygenate synthesis reaction zone may be selected from the approximate range of 20 to 200 bar, more preferably a pressure is employed in the approximate range of 80 to 150 bar. Primarily, the hydrogen and carbon monoxide partial pressures present in stream A should be sufficient to enable the production of the target alcohols. For the purpose of this invention, the term GHSV is the gas hourly space velocity which is the rate of gas flow over the catalyst. It is determined by dividing the volume of gas (at 25° C. and 1 atmosphere) which passes over the catalyst in one hour by the volume of the catalyst.

The optimum gas hourly space velocity (GHSV) of the stream A (liters of stream/hr/liter of catalyst) passing through the reaction zone can vary significantly, depending upon a variety of factors such as, for example, reaction conditions, composition of the stream and age and type of catalyst being used. Preferably, the GHSV can be maintained at any rate in the range of from approximately 1 to 30,000 hr-1, more preferably the GHSV will be maintained at a rate of between approximately 500 hr-1 and 20,000 hr-1, and most preferably the GHSV will be maintained at a rate of approximately between 1,000 hr-1 and 10,000 hr-1.

Whilst the aforementioned reaction conditions specified for the oxygenate synthesis reactor, form preferred embodiments for the present invention, reaction conditions outside of this stated range are not excluded, and the effective reaction conditions may comprise any that are sufficient to produce the aforementioned target alcohols. The exact reaction conditions will be governed by the best compromise between achieving high catalyst selectivity, activity, lifetime and ease of operability, whilst maintaining the intrinsic reactivity of the starting materials, the stability of the starting materials in question and the stability of the desired reaction product.

As previously indicated, the catalyst used in the oxygenate synthesis reactor is preferably a modified molybdenum sulphide based catalyst, or a modified methanol based catalyst and/or a precious metal based catalyst such as a rhodium catalyst, and/or a modified Fischer-Tropsch catalyst.

Molybdenum sulphide based catalysts are preferred; these can be modified by a promoter. Promoter(s) can be added as salts during the catalyst preparation; the preferred promoter(s) are potassium ions and are derived from a salt of potassium, such as potassium carbonate or acetate. The preferred loadings of potassium ions per molybdenum is comprised between 0.7 and 1.5, most preferably between 1.0 and 1.4.

The preferred catalyst, according to the present invention, is a molybdenum sulphide based catalysts containing cobalt, the cobalt to molybdenum molar ratio being preferably comprised between 0.5 and 3.0, more preferably between 0.5 and 1.0, most preferably between 0.5 to 0.9.

According to an embodiment of the present invention, stream B exiting the oxygenate synthesis reactor is subsequently cooled and a separation into a liquid portion and a gaseous portion is conducted. According to a preferred embodiment of the present invention the said separation is conducted using a knockout drum or a dephlegmator at a similar pressure to that used for the oxygenate synthesis reaction.

Subsequently, a C2 and C2+ alcohol(s) and water stream is recovered from the said separated liquid portion to form a stream E (e.g. by conventional distillation). Simultaneously, the said separated gaseous portion from stream B is preferably washed with alcohol, allowing recovery of a $CO_2$ rich stream D and the production of the gaseous part of stream C.

The efficiency of the said alcohol wash can be improved by pre-chilling the alcohol. The said alcohol is preferably taken from the separated liquid portion of stream B. The preferred alcohol used for performing the wash is methanol, which can be obtained via the said conventional distillation of stream B.

The alcohol washing requires good gas/liquid contact. Common methods used include vessel internals which increase internal surface area of contact between liquid and gas, such as packings, structured packings, baffles, sieve plates. Alternatively, said $CO_2$ rich stream D may be recovered by any suitable method(s) known to those skilled in the art, for example, by reacting with amines; by performing a methanol wash (i.e. the RECTISOL process) and/or by using hot potassium carbonate (e.g. the BENFIELD process).

According to the present invention stream C comprises CO, C1-C3 alkanes, hydrogen and methanol. The said methanol comes from the separation of the liquid portion of stream B (post stream E recovery) and/or liquid methanol recovered from the aforementioned $CO_2$ washing.

Additionally, as a consequence of the aforementioned separation some methanol may become entrained together with the CO2 to form a part of stream D; this said methanol may then be recovered to subsequently form a part of stream C. The method used to recover the entrained methanol from stream D may be any one or more of the methods known to those skilled in the art (e.g. by using a H2O wash and/or by using molecular sieves and/or by using refrigeration techniques).

Thus, stream C consists of a gaseous part and a liquid part (under standard temperature and pressure, i.e. 0 C and 101, 325 Pa). The liquid part of stream C contains predominately methanol and may also contain esters and/or ethers. The gaseous part of stream C predominately contains H2, CO, and alkanes (e.g. C1 to C3 alkanes); additionally it may also contain N2.

According to the present invention, at least part of said stream C is reintroduced into the oxygenate synthesis reactor of step 2 preferably by admixing at least part of stream C to treated stream A, prior to entering the oxygenate synthesis reactor.

According to a preferred embodiment of the present invention, after the said admixing of the recycle stream C and the treated stream A, at least of part of the CO2 present is removed, by any suitable means or methods known to those skilled in the art; prior to the stream being introduced into the oxygenate synthesis reactor of step 2. Alternatively at least a part of the said admixed stream may be introduced directly into the separation stage defined by step 3, together with stream B.

The said recycle of stream C, results in an increased ester content in the oxygenate synthesis reactor and the applicants have unexpectedly found that when a certain amount of esters are present in the oxygenate synthesis reactor, there is an overall increase in the yield of the targeted C2 and C2+ alcohol(s). Thus according to a preferred embodiment of the present invention, the preferred quantity of esters (as a molar ratio of the total esters to methanol introduced into the oxygenate synthesis reactor) introduced into the oxygenate synthesis reactor of step 2, is more than 0.1% but less than 10%, preferably more than 0.25% but less than 15% and most preferably more than 0.5% but less than 1%.

According to a further embodiment of the present invention, the said quantity of esters that are present in the oxygenate synthesis reactor, may additionally comprise a separate independent feed of ester(s) (in addition to those esters that are produced inside the oxygenate synthesis reactor and form part of the liquid portion of the stream C recycle) as part of the integrated process. Preferably the esters that are introduced into the oxygenate synthesis reactor are those with 3 or less carbon atoms (i.e. 3 or less carbon atoms in either the alkyl component and/or 3 or less carbon atoms in the carboxylate component of the ester), most preferably the esters that are introduced into the oxygenate synthesis reactor are methyl acetate and/or ethyl acetate.

According to another embodiment of the present invention, the oxygenate synthesis reactor advantageously contains a certain quantity of methanol. However, the preferred quantity of methanol present in the oxygenate synthesis reactor is preferably restricted, as it has been discovered that its presence leads to an increased production of methane and hence, the beneficial effect of methanol addition on productivity reaches a plateau. Therefore, the applicants have found that the preferred quantity of methanol (as a molar ratio of methanol to the total feed entering into the oxygenate synthesis reactor), entering into the oxygenate synthesis reactor is more than 0.25% and less than 10%, preferably more than 0.5% and less than 5% and most preferably more than 0.75% and less than 4%. The methanol may comprise a separate independent feed of methanol, in addition to the said recycled methanol that forms a part of the liquid portion of stream C.

The applicants have unexpectedly found that by implementing this preferred embodiment of separating and recycling the methanol into the oxygenate synthesis reactor as part of the integrated process of the present invention, it was possible to increase the amount of ethanol and propanol(s) produced in the process. Thus, the present invention also provides an improved process for the conversion of hydrocarbons to alcohol(s), in terms of efficiency and selectivity to the target alcohol(s).

According to another embodiment of the present invention, at least part of the methanol that is present in stream C and/or stream E is recovered, by any method or means known to those skilled in the art.

Depending on the feedstock and the selectivity for the conversion of the syngas to alcohol(s), the applicants have discovered an additional embodiment of the present invention, wherein it is advantageous to purge some of steam C to prevent the build up of inert materials present in the oxygenate synthesis reaction, e.g. methane, ethane and N2.

According to the present invention, a fraction of stream C, preferably a fraction of the gaseous part of stream C, is treated and separated into a stream comprising CO and a stream comprising H2 and inert components comprising alkanes and optionally nitrogen. The separated CO is then recycled to the oxygenate synthesis reactor of step 2 together with at least part of the original stream C.

The part of the gaseous part of stream C which is directly recycled into the oxygenate synthesis reactor of step 2 preferably represents from 95 to 30% of the gaseous part of stream C, more preferably from 75 to 50% of the gaseous part of stream C.

The fraction of the gaseous part of stream C (step 4) which is treated and separated preferably represents from 5 to 60% of the gaseous part of stream C, more preferably from 25 to 40% of the gaseous part of stream C.

Preferably the separated hydrogen is recycled into the syngas reactor of step 1. Preferably the separated inert components (with respect to the oxygenate synthesis reaction, e.g. C1-C3 alkanes and optional nitrogen) are used as a fuel, more preferably the inert components are used as a fuel for the furnace of the said syngas reactor.

The fraction of the gaseous part of stream C (step 4) which is treated and separated may also still contain some methanol which is preferably recycled together with the separated CO into the oxygenate synthesis reactor of step 2.

As indicated above, there is a preferred total amount of methanol which is recycled into the oxygenate synthesis reactor of step 2. Consequently, some of the methanol can also advantageously be separated and exported for sale; it can also be used as a feed to the steam reformer of step 1 and/or used as a fuel.

The aforementioned separation of the fraction taken from stream C, into a CO stream and a hydrogen stream and inert components, can be done by any appropriate methods known by those skilled in the art. The said separation can be done in one or several steps. For example, the CO stream can be isolated from the combined H2 and inert components stream, said combined stream being either used as a fuel or then subjected to a further separation stage in order to isolate the H2 from the inert components which would then allow to use the H2 as a feedstock to the SMR. Alternatively, a preferred embodiment of the present invention is to proceed with the separation of the three streams in one step. For example, cryogenic separation can be advantageously used to recover CO and H2, from alkanes and nitrogen. Vacuum swing adsorption can also be used for this separation.

Alternatively, the applicants have unexpectedly found another embodiment in order to prevent the build up of inert materials inside the oxygenate synthesis reactor. This embodiment consists of adding an independent water feed to at least a fraction of stream C, preferably to at least a fraction of the gaseous part of stream C, and subjecting the resulting mixture to a water gas-shift reaction step, in order to convert a majority of the CO present, into CO2 and H2. This then means that the separation of CO2 and H2 from the inert components is economically advantageous in terms of efficiency, by using a simple, yet effective, separation method known to those skilled in the art; for example, the CO2 can first be removed by an alcohol wash and the remaining part of the fraction of stream C can then undergo a membrane separation method to isolate the H2. Alternatively, the original fraction of stream C is directly subjected to a membrane separation method which allows to separate the CO2 and the H2 from the inert components.

Consequently, the recovered H2 and/or CO2 can advantageously be recycled back to the steam reformer of step 1.

Such appropriate membrane technologies can be found in 'Purification and Recovery Options for Gasification' D. J. Kubek, E. Polla, F. P. Wilcher, UOP, 1996, and are hereby incorporated by reference.

Another description of appropriate membrane separation technology is given by "Basic Principles of membrane technology by Marcel Mulder—publisher Kluwer academic publishers 2000, London" ISBN 0=7923-4248-8. Suitable membranes for hydrogen separation include asymmetric or composite membranes with an elastomeric or glassy polymeric top layer. This top layer is typically ~0.1 to a um in thickness. Suitable top layer membrane materials include elastomers such as polydimethylsiloxane, and polymethylpentene, and glassy polymers such as polyimides and polysulphone. Metal membranes such as palladium may also be employed and these are typically operated at elevated temperatures and as such maybe suitable for combined water gas shift and hydrogen recovery as a single unit operation. The driving force for the separation is provided by a pressure drop across the membrane, hydrogen is recovered on the low pressure side and the CO2 and methane and nitrogen mostly retained on the high pressure side. Preferably the membrane material is a glassy polymer. Preferably the pressure drop across the membrane is >5 barg and less than 100 Barg, the temperature of operation is typically ambient to 80 C.

As indicated above, the water gas shift reaction is used to convert carbon monoxide to carbon dioxide and hydrogen through a reaction with water e.g.

$$CO + H_2O = CO_2 + H_2$$

The reaction is exothermic, which means the equilibrium shifts to the right at lower temperatures conversely at higher temperatures the equilibrium shifts in favour of the reactants. Conventional water gas shift reactors use metallic catalysts in a heterogeneous gas phase reaction with CO and steam. Although the equilibrium favours formation of products at lower temperatures the reaction kinetics are faster at elevated temperatures. For this reason the catalytic water gas shift reaction is initially carried out in a high temperature reactor at 350-370 C and this is followed frequently by a lower temperature reactor typically 200-220 C to improve the degree of conversion (Kirk-Othmer 1995, Ullman's 1989). The conversions of CO are typically 90% in the first reactor and a further 90% of the remaining CO is converted in the low temperature reactor. Development of higher activity water gas shift catalysts will allow reduction in the reaction temperatures employed. Other non metallic catalysts such as oxides and mixed metal oxides such as Cu/ZnO are known to catalyse this reaction. The degree of conversion of the CO can also be increased by adding more than the stoichiometric amount of water but this incurs an additional heat penalty. Methane and nitrogen are inert under typical water gas shift conditions. Then, at least a fraction of stream C is fed to a water gas shift reactor together with steam, preheated to the reaction temperature and contacted with the catalyst, a second low temperature water gas shift reactor is optionally employed on the cooled exit gas from this reactor.

Thus, according to another embodiment of the present invention, there is provided a process for the conversion of a hydrocarbon feedstock into alcohol(s), wherein the hydrocarbons are first converted into syngas, which is subsequently converted into alcohols, characterised by the following consecutive steps:
1) converting a hydrocarbon feedstock, in a syngas reactor, into a stream A, comprising essentially of a mixture of carbon oxide(s) and hydrogen,
2) converting at least part of stream A, in the presence of a catalyst in a oxygenate synthesis reactor under a temperature comprised between 150 and 400° C. and a pressure of 20 to 200 bar, into an alcohols stream B, comprising essentially methanol, ethanol, propanol(s), H2, C1-C3 alkanes, CO, CO2 and water,
3) separating stream B, into a stream C containing the CO, C1-C3 alkanes, H2 and methanol; a stream D containing the CO2; and recovering a stream E containing the ethanol, propanol(s) and water,
4) adding water to at least a fraction of stream C and subjecting the resulting mixture to a water gas-shift reaction step in order to convert a majority of the CO present into CO2 and H2,
5) separating the C1-C3 alkanes from the CO2 and H2 stream of step 4,
6) recycling the H2 and CO2 stream from step 5 into the steam reformer of step 1,
7) reintroducing at least part of stream C into the oxygenate synthesis reactor of step 2, and
8) reintroducing at least part of stream D into the syngas reactor of step 1.

As indicated above, the water gas-shift reaction step 4) is preferably performed on a fraction of the gaseous part of stream C only. The part of the gaseous part of stream C which is directly recycled into the oxygenate synthesis reactor of step 2 preferably represents from 95 to 30%, more preferably from 83 to 50% of the gaseous part of stream C.

The fraction of the gaseous part of stream C (step 4) which is subjected to the WGS treatment of step 4 preferably represents from 5 to 60% of the gaseous part of stream C, more preferably from 17 to 40% of the gaseous part of stream C.

According to the present invention, the said CO2 rich stream D produced in step 3, is preferably compressed and at least part of the stream is recycled back to the syngas reactor of step 1, as a means of adjusting the syngas ratio of stream A to the optimum ratio required for the oxygenate synthesis reaction. Therefore, the CO2 produced during the separation of stream B (step 3) is not released to the atmosphere and may be utilised in an environmentally efficient manner as well as improving the overall economics of the system.

The applicants have unexpectedly found that an additional independent CO2 import may be required in order to provide the optimum syngas ratio for the oxygenate synthesis reaction. The quantity of CO2 that needs to be imported into stream D is between 0.02 and 1 TONNE(S) of CO2 per TONNE of C2 and C3 alcohol(s) produced, more preferably between 0.1 and 0.5 TONNES of CO2 per TONNE of C2 and C3 alcohol(s) produced and is most preferably 0.38 TONNES of CO2 per TONNE of C2 and C3 alcohol(s) produced. In practice, the optimum quantity of CO2 imported will vary depending on the feedstock used for the syngas generation and for the steam reforming furnace. For example, when hydrogen is used to fuel the furnace(s), the overall CO2 emissions for the process will reach a minimum.

Indeed, importing CO2 quantities outside of the above stated ranges are also included, however they do not form preferred embodiments of the present invention, since the applicants have found that when using a certain feedstock to fuel the furnace (e.g. hydrocarbons), introducing levels of CO2 above those stated above into stream D can lead to the undesirable effect of increasing the overall dilute CO2 emissions for the process.

The process according to the present invention has been found to be highly beneficial towards alcohol(s) selectivity, especially towards ethanol selectivity, whilst simultaneously significantly reducing overall CO2 emissions and improving on the overall heat efficiency associated with conventional processes.

Beyond these advantages, the present process invention has also been found to encompass the following unexpected advantages, amongst others:
  (i) less waste, and thus higher carbon efficiency.
  (ii) reduced methane production.
  (iii) improved economics, fewer separations, reduced storage tanks.
  (iv) no corrosion and metallurgy constraints due to the potential hydrolysis of the esters during subsequent purification and storage stages.

The invention claimed is:

1. Process for the conversion of a hydrocarbon feedstock into alcohol(s), wherein the hydrocarbons are first converted into syngas, which is subsequently converted into alcohols, comprising the following consecutive steps:
  1) converting a hydrocarbon feedstock, in a syngas reactor, into a stream A, comprising essentially of a mixture of carbon oxide(s) and hydrogen,
  2) converting at least part of stream A, in the presence of a catalyst in a oxygenate synthesis reactor under a temperature comprised between 150 and 400° C. and a pressure of 20 to 200 bar, into an alcohols stream B, comprising essentially methanol, ethanol, propanol(s), H2, C1-C3 alkanes, CO, CO2 and water,
  3) separating stream B, into a stream C containing the CO, C1-C3 alkanes, H2 and methanol; a stream D containing the CO2; and recovering a stream E containing the ethanol, propanol(s) and water,
  4) treating a fraction of stream C in order to separate said fraction into a stream comprising CO, and a stream comprising H2 and the C1-C3 alkanes,
  5) reintroducing at least part of stream C together with the stream comprising CO from step 4 into the oxygenate synthesis reactor of step 2, and
  6) reintroducing at least part of stream D into the syngas reactor of step 1.

2. Process for the conversion of a hydrocarbon feedstock into alcohol(s), wherein the hydrocarbons are first converted into syngas, which is subsequently converted into alcohols, comprising the following consecutive steps:
  1) converting a hydrocarbon feedstock, in a syngas reactor, into a stream A, Comprising essentially of a mixture of carbon oxide(s) and hydrogen,
  2) converting at least part of stream A, in the presence of a catalyst in a oxygenate synthesis reactor under a temperature comprised between 150 and 400° C. and a pressure of 20 to 200 bar, into an alcohols stream B, comprising essentially methanol, ethanol, propanol(s), H2, C1-C3 alkanes, CO, CO2 and water,
  3) separating stream B, into a stream C containing the CO, C1-C3 alkanes, H2 and methanol; a stream D containing the CO2; and recovering a stream E containing the ethanol, propanol(s) and water,
  4) adding water to at least a fraction of stream C and subjecting the resulting mixture to a water gas-shift reaction step in order to convert a majority of the CO present into CO2 and H2,
  5) separating the C1-C3 alkanes from the CO2 and H2 stream of step 4,
  6) recycling the H2 and CO2 stream from step 5 into the syngas reactor of step 1,
  7) reintroducing at least part of stream C into the oxygenate synthesis reactor of step 2, and
  8) reintroducing at least part of stream D into the syngas reactor of step 1.

3. A process according to claim 1, wherein the syngas reactor of step 1 is a steam reformer and steam is fed into the said reactor together with the hydrocarbon feedstock.

4. A process according to claim 1, wherein the synthesis gas molar ratio, defined as being H2/CO, of the total feed introduced into the oxygenate synthesis reactor of step 2, is comprised between 0.5 and 2.0.

5. A process according to claim 1, wherein the alcohol(s) produced in the oxygenate synthesis reactor of step 2, are primarily methanol, ethanol, propanol(s) (n-propanol with low amounts of iso-propanol), and butanol(s) (n-butanol and iso-butanol) and represent together at least 50% by carbon content of the products, where the products are defined as being all products excluding CO2 and CO, obtained from the oxygenate synthesis reactor (stream B).

6. A process according to claim 1, wherein the conversion of the carbon oxide(s) per pass through the oxygenate synthesis reactor is between 5 and 70%.

7. A process according to claim 1, wherein recycle stream C comprises a liquid part containing methanol, esters and/or ethers, and a gaseous part containing hydrogen, CO, nitrogen and C1 to C3 alkanes.

8. A process according to claim 7, wherein the quantity of esters, calculated as a molar ratio of the total esters to methanol introduced into the oxygenate synthesis reactor, introduced into the oxygenate synthesis reactor of step 2, are more than 0.1% but less than 10%.

9. A process according to claim 7, wherein the esters that are recycled into the oxygenate synthesis reactor are those with 3 or less carbon atoms in either the alkyl component and/or 3 or less carbon atoms in the carboxylate component of the ester.

10. A process according to claim 1 wherein the separated hydrogen from step 4 is recycled back to syngas reactor of step 1 together with the CO2 recycle stream D.

11. A process according to claim 1 wherein the separated inert components (C1-C3 alkanes and nitrogen) of step 4 are used as a fuel.

12. A process according to claim 1 wherein step 4 is performed on the gaseous part of stream C.

13. A process according to claim 2 wherein the syngas reactor of step 1 is a steam reformer and steam is fed into the said reactor together with the hydrocarbon feedstock.

14. A process according to claim 1 wherein the synthesis gas molar ratio, defined as being H2/CO, of the total feed introduced into the oxygenate synthesis reactor of step 2 is comprised between 0.5 and 1.5.

15. A process according to claim 1 wherein the alcohol(s) produced in the oxygenate synthesis reactor of step 2 are primarily methanol, ethanol, propanol(s) (n-propanol with low amounts of iso-propanol), and butanol(s) (n-butanol and iso-butanol) and represent together at least 75% by carbon content of the products where the products are defined as being all products excluding CO2 and CO obtained from the oxygenate synthesis reactor (stream B).

16. A process according to claim 1 wherein the alcohol(s) produced in the oxygenate synthesis reactor of step 2 are primarily methanol, ethanol, propanol(s) (n-propanol with small amounts of iso-propanol) and butanol(s) (n-butanol and iso-butanol) and represent together at least 80% by carbon content of the products, where the products are defined as being all products excluding CO2 and CO, obtained from the oxygenate synthesis reactor (stream B).

17. A process according to claim 1 wherein the conversion of the carbon oxide(s) per pass through the oxygenate synthesis reactor is between 10 and 50%.

18. A process according to claim 1 wherein the conversion of the carbon oxide(s) per pass through the oxygenate synthesis reactor is between 15 and 40%.

19. A process according to claim 7, wherein the quantity of esters, calculated as a molar ratio of the total esters to methanol introduced into the oxygenate synthesis reactor, introduced into the oxygenate synthesis reactor of step 2, are more than 0.25% but less than 15%.

20. A process according to claim 7, wherein the quantity of esters calculated as a molar ratio of the total esters to methanol introduced into the oxygenate synthesis reactor, introduced into the oxygenate synthesis reactor of step 2, are more than 0.5% but less than 1%.

21. A process according to claim 7, wherein the esters that are introduced into the oxygenate synthesis reactor are methyl acetate and/or ethyl acetate.

22. A process according to claim 11, wherein the separated inert components (C1-C3 alkanes and nitrogen) of step 4 are used as fuel for the furnace used to preheat the hydrocarbon feedstock entering into the syngas reactor.

* * * * *